US012742145B2

(12) United States Patent
Lee et al.

(10) Patent No.: US 12,742,145 B2
(45) Date of Patent: Sep. 22, 2026

(54) ROTOR MIXER FOR AGITATION OF FLUIDS DURING SAMPLE PREPARATION

(71) Applicant: Siemens Healthcare Diagnostics Inc., Tarrytown, NY (US)

(72) Inventors: Alex Hofai Lee, Fremont, CA (US); Daniel Chu, Hercules, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1238 days.

(21) Appl. No.: 17/640,483

(22) PCT Filed: Aug. 18, 2020

(86) PCT No.: PCT/US2020/046743
§ 371 (c)(1),
(2) Date: Mar. 4, 2022

(87) PCT Pub. No.: WO2021/055123
PCT Pub. Date: Mar. 25, 2021

(65) Prior Publication Data

US 2022/0333058 A1 Oct. 20, 2022

Related U.S. Application Data

(60) Provisional application No. 62/903,069, filed on Sep. 20, 2019.

(51) Int. Cl.
*C12M 1/00* (2006.01)
*B01L 3/00* (2006.01)
(Continued)

(52) U.S. Cl.
CPC ........... *C12M 47/06* (2013.01); *B01L 3/5085* (2013.01); *C12N 15/1013* (2013.01);
(Continued)

(58) Field of Classification Search
CPC ...... B01L 3/5085; B01L 7/52; C12N 15/1013
See application file for complete search history.

(56) References Cited

U.S. PATENT DOCUMENTS 8,691,149 B2 4/2014 Fritchie et al.
9,428,746 B2 8/2016 Holmberg et al.
(Continued)

FOREIGN PATENT DOCUMENTS

CN 102027367 4/2011
CN 103540518 1/2014
(Continued)

OTHER PUBLICATIONS

Zhang, Kaihui:"Research progress of the new generation magnetic bead-based nucleic acid automated extraction instrument"; Experimental Research, 49(4), pp. 53-56, Aug. 31, 2019, English Abstract Abstract Only.

(Continued)

*Primary Examiner* — David C Mellon

(57) ABSTRACT

An apparatus, multi-well plate and method for automated cell lysis and nucleic acid purification and processing. The plate includes a lysis well, at least one wash well, and an elution well. The apparatus includes a vertically aligned rotor mixer comprising a magnetic tip and actuators for moving the rotor mixer in a vertical and horizontal directions, to transfer magnetic beads from well to well. The rotor mixer is used to vortex lysis mixtures, wherein the vortexing speed is sufficient to overcome the magnetic attraction between the beads and mixer tip and disperse the beads in solution, to collect nucleic acids such as DNA.

9 Claims, 9 Drawing Sheets

(51) Int. Cl.
*B01L 7/00* (2006.01)
*C12N 15/10* (2006.01)
*G01N 35/00* (2006.01)

(52) U.S. Cl.
CPC ............ *G01N 35/0098* (2013.01); *B01L 7/52* (2013.01); *B01L 2200/0668* (2013.01); *B01L 2400/043* (2013.01); *G01N 2035/00534* (2013.01)

(56) References Cited

U.S. PATENT DOCUMENTS

2002/0008053 A1 1/2002 Hansen et al.
2004/0171169 A1* 9/2004 Kallury ................ G01N 1/4005 436/178
2011/0092691 A1 4/2011 Euting et al.
2013/0034845 A1 2/2013 Kelso et al.
2013/0135394 A1 5/2013 Saikawa et al.
2013/0196422 A1 8/2013 Wilson et al.
2015/0079601 A1 3/2015 Slepnev et al.
2015/0165491 A1* 6/2015 Peter .................. G01N 35/0098 134/25.1
2018/0169658 A1 6/2018 Lei et al.

FOREIGN PATENT DOCUMENTS

CN 106591297 4/2014
CN 103820431 5/2014
CN 103897987 7/2014
CN 104762193 7/2015
WO 2018022689 2/2018

OTHER PUBLICATIONS

Liu et al: "Preparation of Silicon Magnetic Microspheres and Its Application in Nucleic Acid Extraction"; Journal of Shandong Agricultural University (Natural Science Edition); vol. 54; No. 3; Jun. 30, 2023, with English Abstract Abstract Only.
International Search Report for PCT/Us2020/046743 dated Jan. 7, 2021.

* cited by examiner 107
402
104

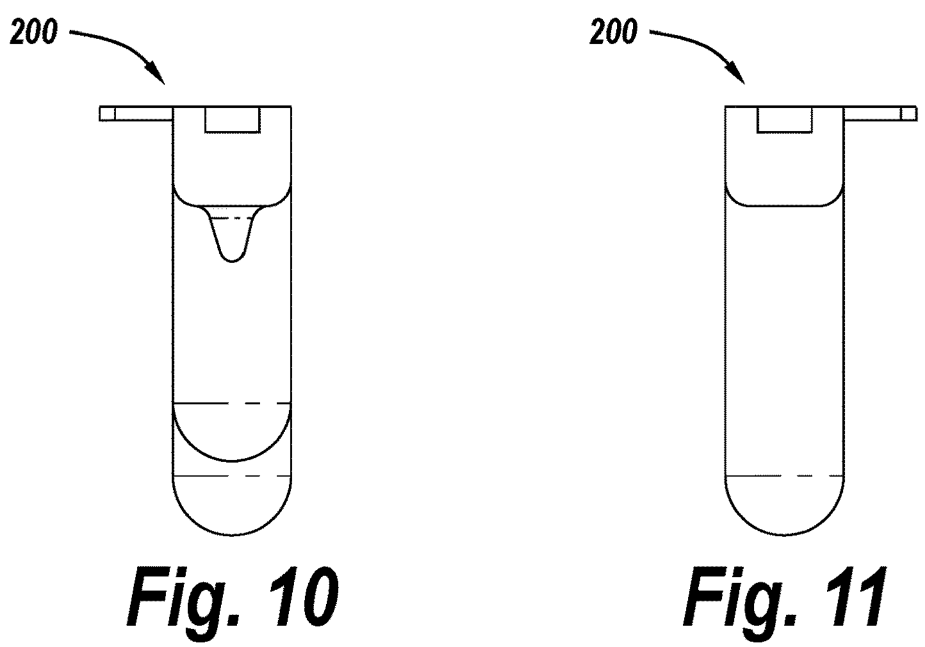
Fig. 10
Fig. 11
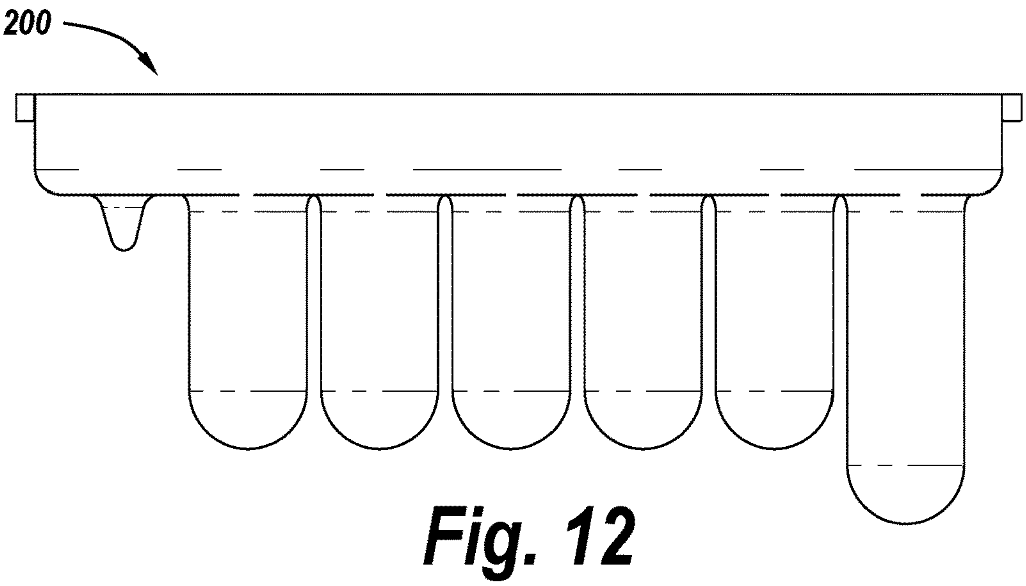
Fig. 12
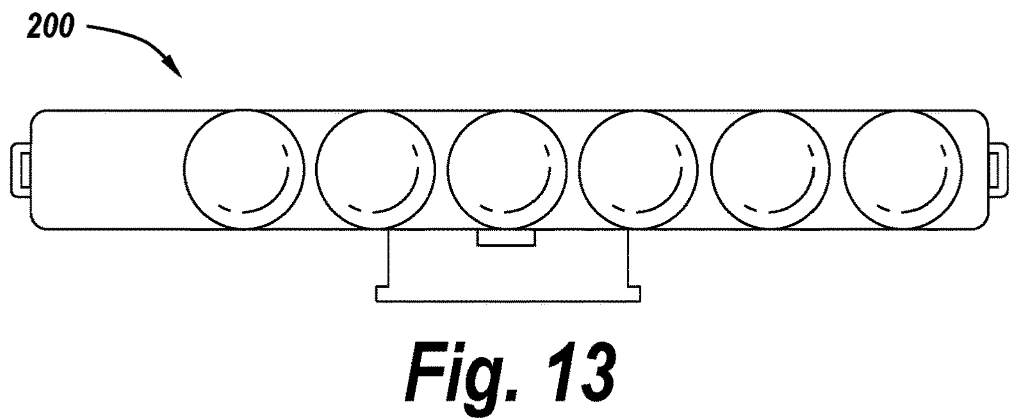
Fig. 13

ROTOR MIXER FOR AGITATION OF FLUIDS DURING SAMPLE PREPARATION

CROSS-REFERENCE TO RELATED APPLICATIONS

N/A

FIELD OF THE DISCLOSURE

The disclosure herein relates generally to the field of cell lysing and nucleic acid purification and isolation. More particularly, the present disclosure relates to a novel rotor mixer and multi-well tray having particular utility in the field of nucleic acid extraction in molecular diagnostics.

BACKGROUND

In a typical cell lysis and nucleic acid isolation protocol using magnetic beads, a sample is moved by a pipette system to a well within a multi-well plate along with a cell lysis buffer and by a quantity of magnetic beads. The beads are functionalized, for example with silica surfaces, to allow selective binding of nucleic acid molecules such as DNA. A succession of mixing by external vibration, magnetic bead separation, supernatant aspiration, and dilution/washing steps are repeated with respect to the well. Heating of one or more of the wells of the multi-well plate may also be employed to facilitate lysis and/or binding. The sample transfer, washing, and elution steps require separate aspiration and dispensing tips to avoid cross-contamination.

Due to the common platform for processing multiple samples, heating and time of heating is limited and not customizable. A single overhead pipetting system is typically responsible for processing all samples within the multi-well plate.

An alternative system and technique involves the use of a magnet disposed within a sealed probe. The probe is selectively disposed within a respective well to allow the magnetic beads to be attracted to the probe by the magnet located within. In one embodiment, the probe may be removed from one well and inserted into fluid within another well. The magnet may then be extracted from within the probe, thus releasing the magnetic beads to be released from the probe surface. Further processing may then follow.

In the field of molecular diagnostics, there is a need for an efficient and cost-effective system and method for lysing cells and purifying samples for amplicon detection.

SUMMARY

In order to overcome the inflexibility and expense of the prior art automated processes for cell lysis and purification, the present disclosure provides a new rotor mixer featuring a magnetic tip. The rotor generates a vortex for combining a biological sample with a lysis buffer and magnetic beads, to form a lysis mixture in a lysis well. To optimize nucleic acid absorption on the magnetic beads, the vortexing speed is sufficient to overcome the magnetic attraction between the beads and the magnetic tip of the rotor mixer and allow the beads to disperse freely in the lysis mixture. When vortexing stops, the beads reattach to the magnetic tip. As a result, the rotor tip can be used to transfer the beads from the lysis mixture to and between other wells where they undergo washing and finally elution of the nucleic acids collected from the sample lysate.

As compared to traditional laboratory vortexing equipment using external vibration of sample wells, the rotor mixer with a magnetic tip provides an efficient, easy and reliable means for transferring magnetic beads between wells, and this setup is particularly suitable to automated sample preparation techniques.

Also provided for use with the rotor mixer is a disposable multi-well plate having a series of open fluid wells. A first well serves as lysis vessel where the lysis mixture is processed by rotor-induced vortexing and the magnetic beads bind to nucleic acid molecules. Other wells serve as washing vessels where the beads are treated with wash buffer to remove undesired lysis mixture residue. In a last, elution well, the washed beads are immersed in elution buffer to collect the nucleic acid molecules from the original sample lysate. Provision is also made for selective, customizable direct heating of one or more of the lysis well and elution well to enhance lysing and/or elution, if desired.

The present system and method enable the provision of multi-well plates with wells preloaded with buffers by the manufacturer, thereby speeding up the overall process and diminishing the likelihood of operator error. Alternatively, multiple trays may be provided in bulk, in a stacked configuration, optionally with each lysis well having respective preloaded magnetic beads.

Other unique features of the presently disclosed system and method include the provision of a disposable protective sleeve to protect the magnetic tip of the rotor during vortexing and other steps of nucleic acid isolation processes. Optionally, the protective sleeve may be fitted by vortex-increasing features such as propeller-shaped projections or paddles.

BRIEF DESCRIPTION OF THE DRAWINGS

Illustrative embodiments of the disclosed technology are described in detail below with reference to the attached drawing figures, which are incorporated by reference herein and wherein:

FIG. 10 is a rear view of the of the multi-well plate of FIG. 7;

FIG. 11 is front view of the multi-well plate of FIG. 7;

FIG. 12 is a side view of the multi-well plate of FIG. 7;

FIG. 13 is a bottom view of the multi-well plate of FIG. 7; and

DETAILED DESCRIPTION

Disclosed herein is an apparatus for extracting nucleic acids such as DNA molecules from biological samples. Use of the presently disclosed and described apparatus enables simplified, easy, and reliable transfer of magnetic beads between wells in a fashion particularly suitable to automated sample preparation techniques.

Figure 1:
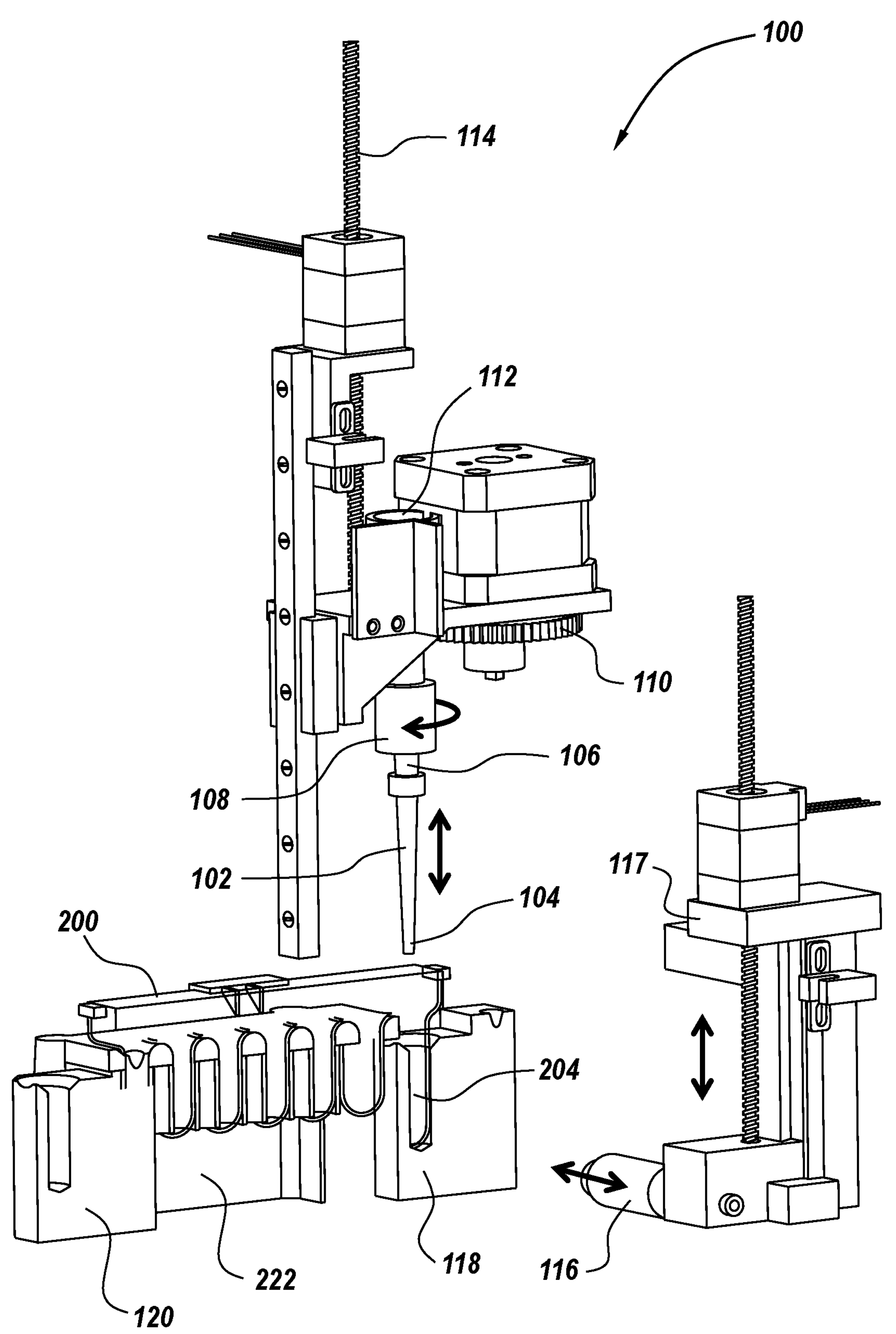
FIG. 1 is a perspective view of a sample lysis and nucleic acid extraction apparatus according to the present disclosure.

FIG. 1 illustrates an exemplary embodiment of an apparatus 100 according to the present disclosure. The apparatus 100 is comprised of a rotor mixer 102 having a magnetic tip 104, such as a ferromagnetic material enclosed within an inert polymeric coating, connected to rotor hub 108 via rotor shaft 106. A disposable protective sleeve, in this instance conically-shaped transparent plastic sleeve 107 shown in FIG. 2, protects magnetic tip 104 and rotor shaft 106 from the contents of buffers and mixtures that are used in nucleic acid extraction. Rotor engine 110 powers rotor mixer 102 when vortexing mixtures of fluids and other components such as magnetic beads. When the rotor mixer 102 is not vortexing, the beads magnetically attach to magnetic tip 104. Hence, when one of the steps of a nucleic acid isolation process is completed, the beads attached to the magnetic tip 104 can be easily transferred to another vessel where the next step is carried out. To this end, the apparatus is fitted with a vertical actuator 112 configured to move rotor mixer 102 in an upwardly or downwardly direction along vertical rail 114 and with a horizontal actuator (not shown) for repositioning the rotor mixer 102 from a vessel to another. In addition, the apparatus 100 may include an external magnet 116 that may be selectively translated to and away from a side wall of a vessel in order to attract and release, respectively, magnetic beads disposed within a vessel. The external magnet may also be selectively, vertically translated relative to the vessel, as will be discussed subsequently.

The vessels may be provided in the form of process wells in a disposable multi-well plate or holder for use in cell lysing and nucleotide purification. Use of the presently disclosed and described multi-well plate enables simplified and faster cell lysis and nucleotide extraction as compared to currently practiced methods. FIGS. 7-13 illustrate an embodiment of a multi-well plate 200 having a body member and a plurality of wells extending in a downwardly direction from the floor of the body member, according to the present disclosure. In this embodiment, the body member is a channel 202 and the process wells include a lysis well 204, wash wells 206, 208, 210, 212, 214, and elution well 216. The channel may help inhibit the unintended flow of working fluid off the multi-well plate.

Lysis well 204 is disposed at a first end 201 of the multi-well plate while the wash wells are disposed intermediate the first end and an opposite second end 203 where elution well 216 is located. Each well extends in a substantially orthogonal direction from the floor of the channel 202 and has an interior volume communicating with the channel via an aperture in the channel floor. The illustrated apertures are circular and coplanar with the floor surface, although embodiments of differing shapes and orientations are also contemplated. The apertures are also substantially colinear along the floor surface and are centered about a longitudinal axis 218 of the multi-well plate.

In one embodiment, the wells are pre-filled with appropriate buffers and other components and then sealed off, for example with a peel-away layer that is removed at the time of use. In another embodiment, the wells each have a tapered lower extent. This enables multiple multi-well plates to be vertically stacked, whereby the outer surface of a lysis well of a first holder is received within the lysis well of a lower, second holder. Similarly, the outer surfaces of the wash wells of the first holder are each received within a respective wash well of the lower, second holder.

In order to optimize vortexing and bead collection performance, the lower extent of lysis well 204 may have a geometry capable of receiving the magnetic tip 104. As seen for example in the side section view of FIG. 8, lysis well 204 may have a larger volume than the wash wells in order to provide sufficient space for the biological sample, lysis buffer, and magnetic beads. Conversely, elution well 216 may have a smaller volume than the wash wells in order to minimize dilution of the final nucleic acid product and may be characterized by a conical cross-section to facilitate removal of the product with a pipettor or other devices for transferring fluids.

The lysis well 204 of the multi-well plate 200 may be subjected to heating, depending upon the characteristics of the lysis process implemented therewith. For example, the outer surface of the lower extent of the lysis well 204 may be configured to be received within a heater external to the unitary structure. Such a heater may be a heating block 118 placed beneath the holder, receiving the outer surface of the lower extent of the lysis well therewithin for a required or desired time period. Similarly, the elution well 216 of the multi-well plate 200 may be heated with another heater external to the unitary structure, such as heating block 120, depending upon the elution process implemented therewith.

The multi-well plate 200 may be provided with retention features, such as tab 220 projecting from the upper rim of channel 202 or other lateral projections extending from the multi-well plate on either side of the multi-well plate 200. During processes such as heating and vortexing, when external devices move relative to the multi-well plate 200, the retention features may be selectively engaged by external gripping mechanisms, thereby maintaining the multi-well plate in a fixed position relative to the external devices. The retention features may also be of use during the introduction of samples, buffers, beads or other components in the wells or eluted product retrieval as a pipetting system presses down on the inner surface of the elution well 216. Alternatively, the multi-well plate and associated heating blocks and support structures, i.e., the plate holder 222, may be configured for lateral, horizontal translation relative to the rotor mixer 102, thus obviating the need for enabling horizontal translation of the rotor mixer and associated components.

A non-limiting exemplary method of using the system of FIG. 1 in combination with the multi-well plate of FIGS. 7-13 is now described in conjunction with FIGS. 2-6 and 14. Not all steps need be practiced in the order described below, nor be utilized at all, depending upon the embodiment. First, in step 300, a multi-well plate such as described in the foregoing is provided and placed into plate holder 222. In step 302, one or more wash buffers are loaded into the wash wells, an elution buffer is loaded into elution well 216, and lysis buffer is loaded into the lysis well 204.

Magnetic beads 402 are also introduced in the lysis well 204, as at step 304. In one example, the material of the beads may be optimized for genomic DNA extraction from blood samples, but its composition may vary to suit other types of bodily fluids or tissues or for extracting other types of nucleic acids such as RNA. A biological sample is then loaded into the lysis well (step 306), yielding a lysis mixture ready for vortexing. Typical samples include blood, sputum, hair, and other bodily fluids and tissues, optionally pretreated for example by freezing, homogenizing, or grinding. Those of skill in the art will recognize that the choice of buffers and other reactants may vary according to the type of sample and beads to provide optimal conditions for nucleic acid extraction. While this illustrated process depicts a certain order of loading the lysis well to form the lysis mixture, other orders may be employed, such as disposing the sample into the lysis well prior to adding the magnetic beads.

Figure 2:
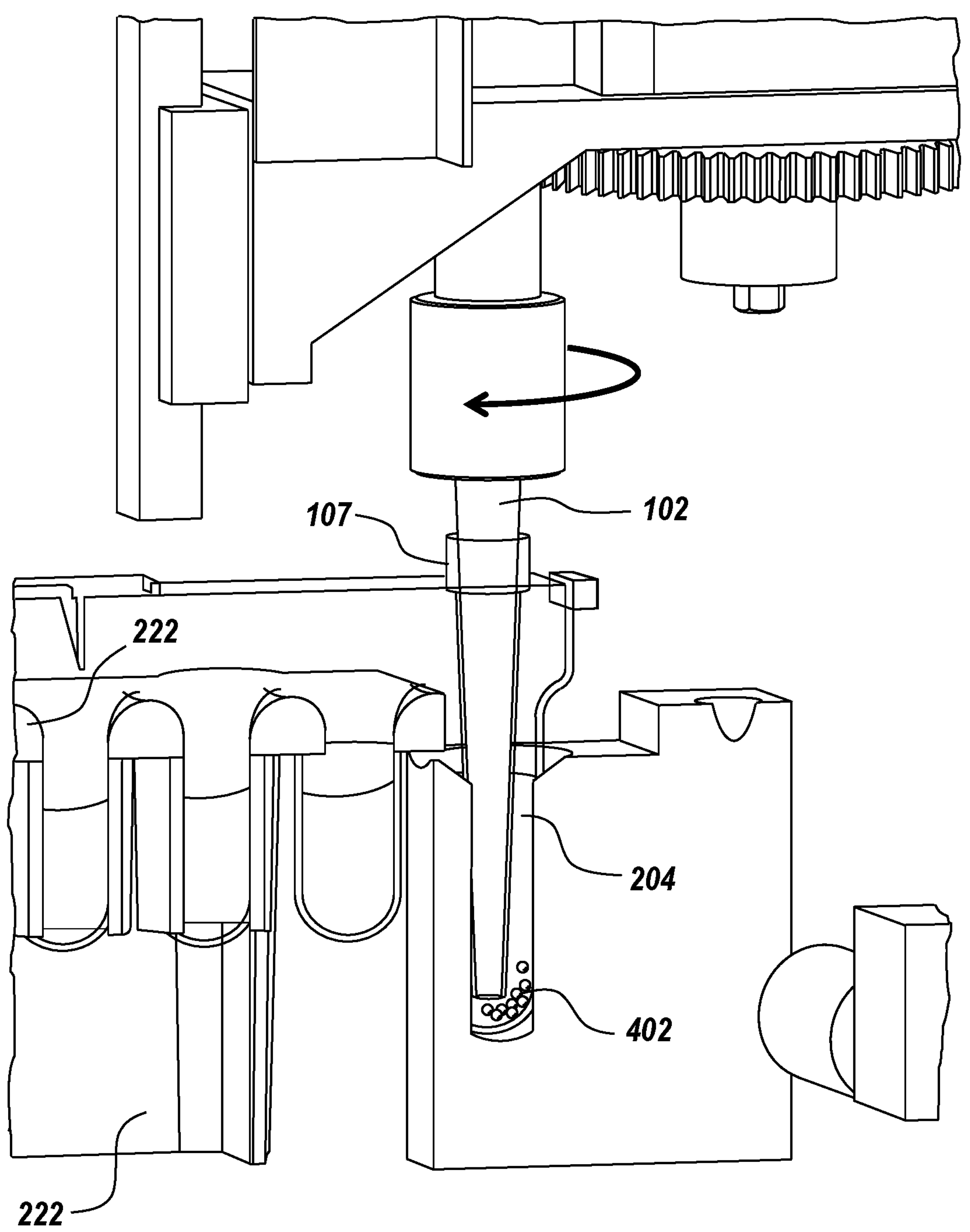
FIG. 2 illustrates vortexing of a lysis mixture by the apparatus of FIG. 1 in the presence of magnetic beads.

In step 308, the lysis mixture is vortexed by spinning the rotor mixer 102, as exemplified in FIG. 2, either continuously or intermittently. For at least a portion of the vortexing step, the rotor mixer 102 is spun at a rate sufficient to overcome attraction forces between magnetic beads 402 and magnetic tip 104, thereby freeing the beads to swirl about the lysis mixture and bind to nucleic acid molecules dispersed therein following cell lysis. In an exemplary embodiment, the rotor mixer spins at about 5,000 to about 10,000 revolutions per minute.

Figure 3:
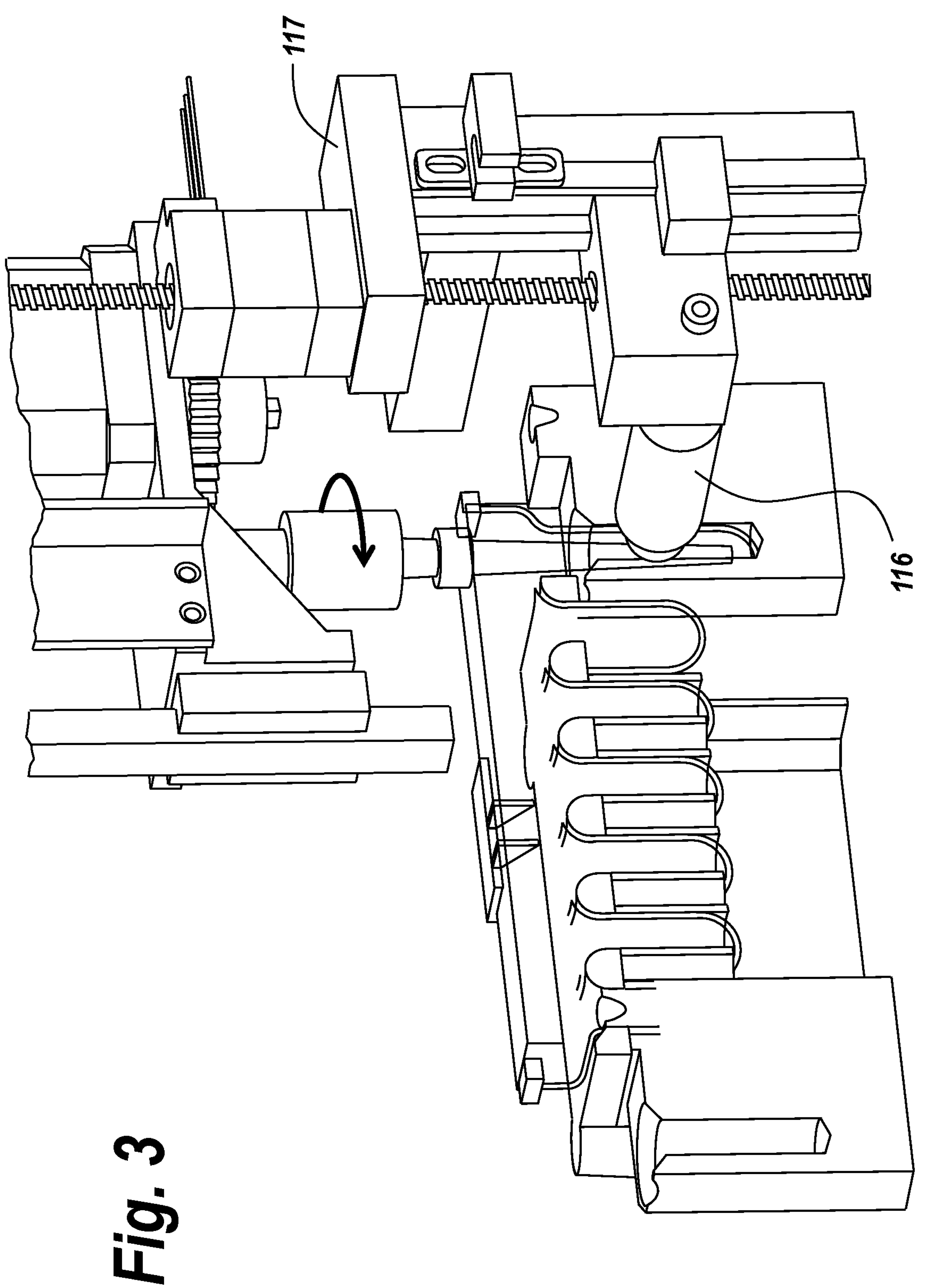
FIG. 3 illustrates the application of an external magnetic field to the lysis well of a multi-well plate.
Figure 4:
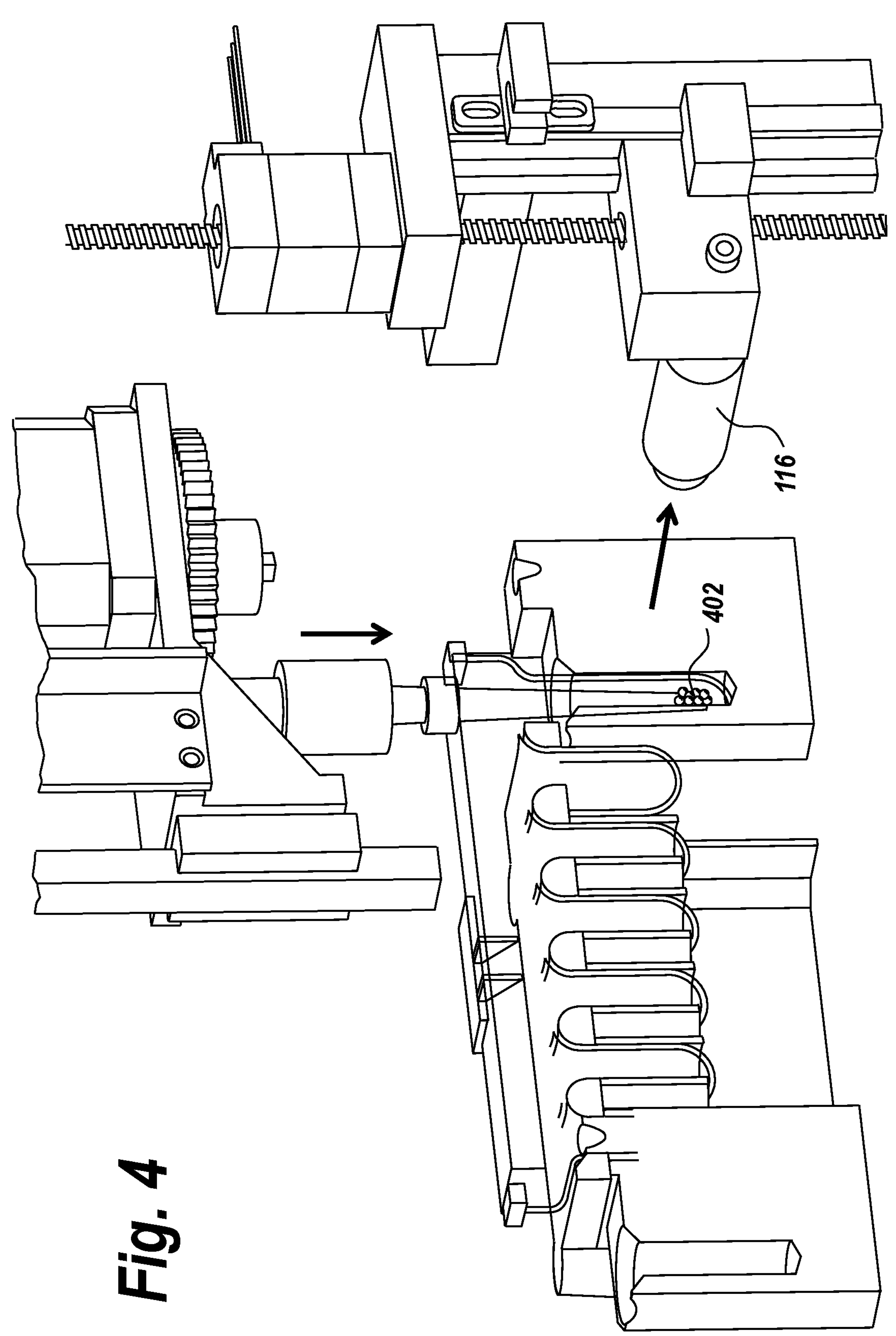
FIG. 4 illustrates removing the external magnetic field of FIG. 3 from the multi-well plate and lowering the magnetic tip, to collect the beads.

When vortexing ceases, magnetic beads 402 attach to magnetic tip 104. In instances where some or all the beads fail to attach and remain afloat or absorbed to the well wall, external magnet 116 may be translated to a side wall of lysis well 204 by operation of translation member 117 (FIG. 3). The rotor mixer 102 is temporarily moved upwards to a higher level of the lysis mixture, while the magnetic field exerted by external magnet 116 on the outer surface of the well forms the beads 402 into a cluster adhering to the well wall. External magnet 116, still pressed against the side of lysis well 204, is moved by the translation member first downwards, then away from well wall (FIG. 4), thereby removing its magnetic field and leaving the beads 402 resting at the bottom of well 204 and ready for collection (step 310). The rotor mixer is then lowered into the lysis well 204 whereby the beads 402 are gathered against the magnetic tip 104.

Figure 5:
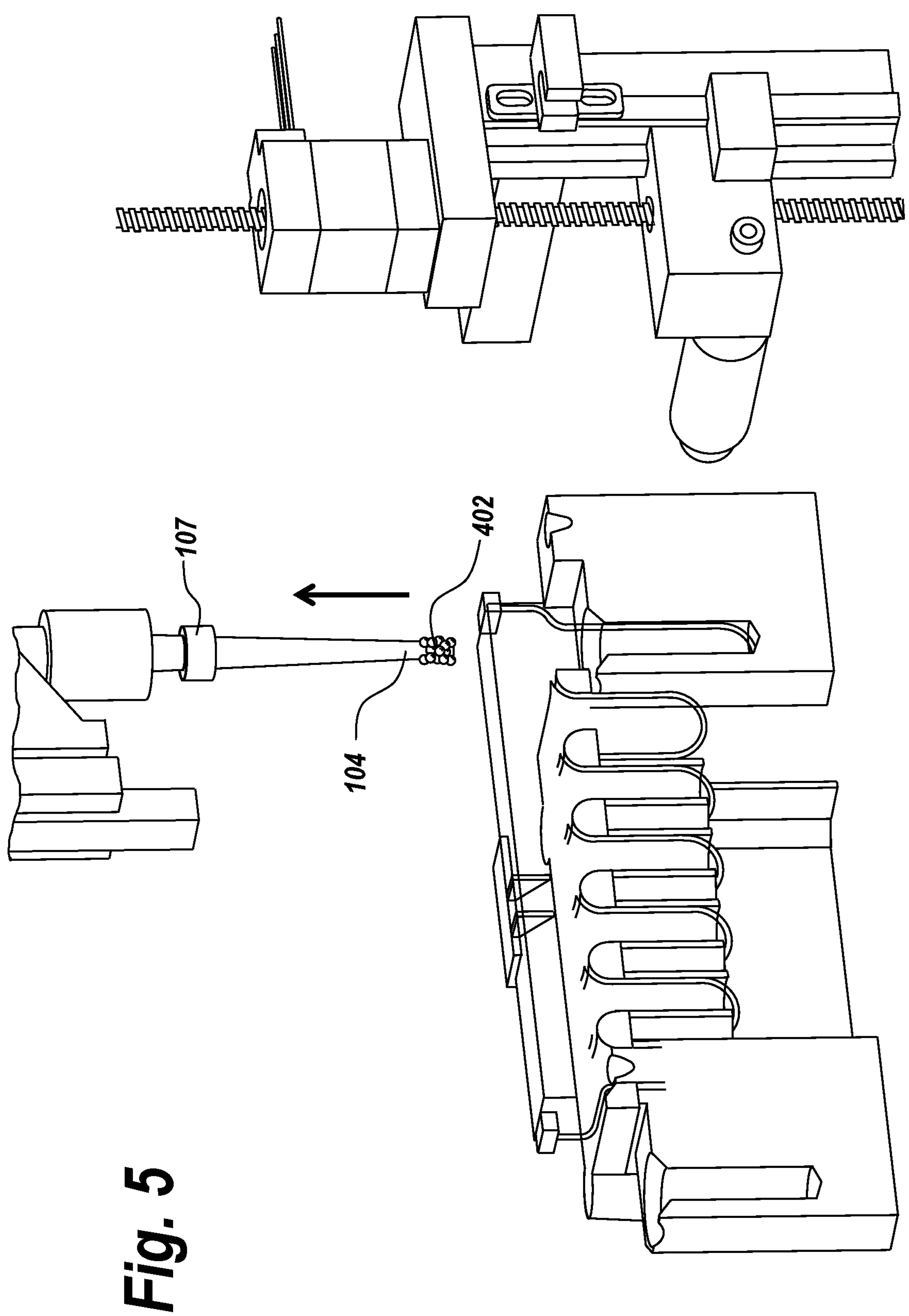
FIG. 5 illustrates removing the rotor mixer tip with the magnetic beads magnetically attached thereto from the lysis well.
Figure 6:
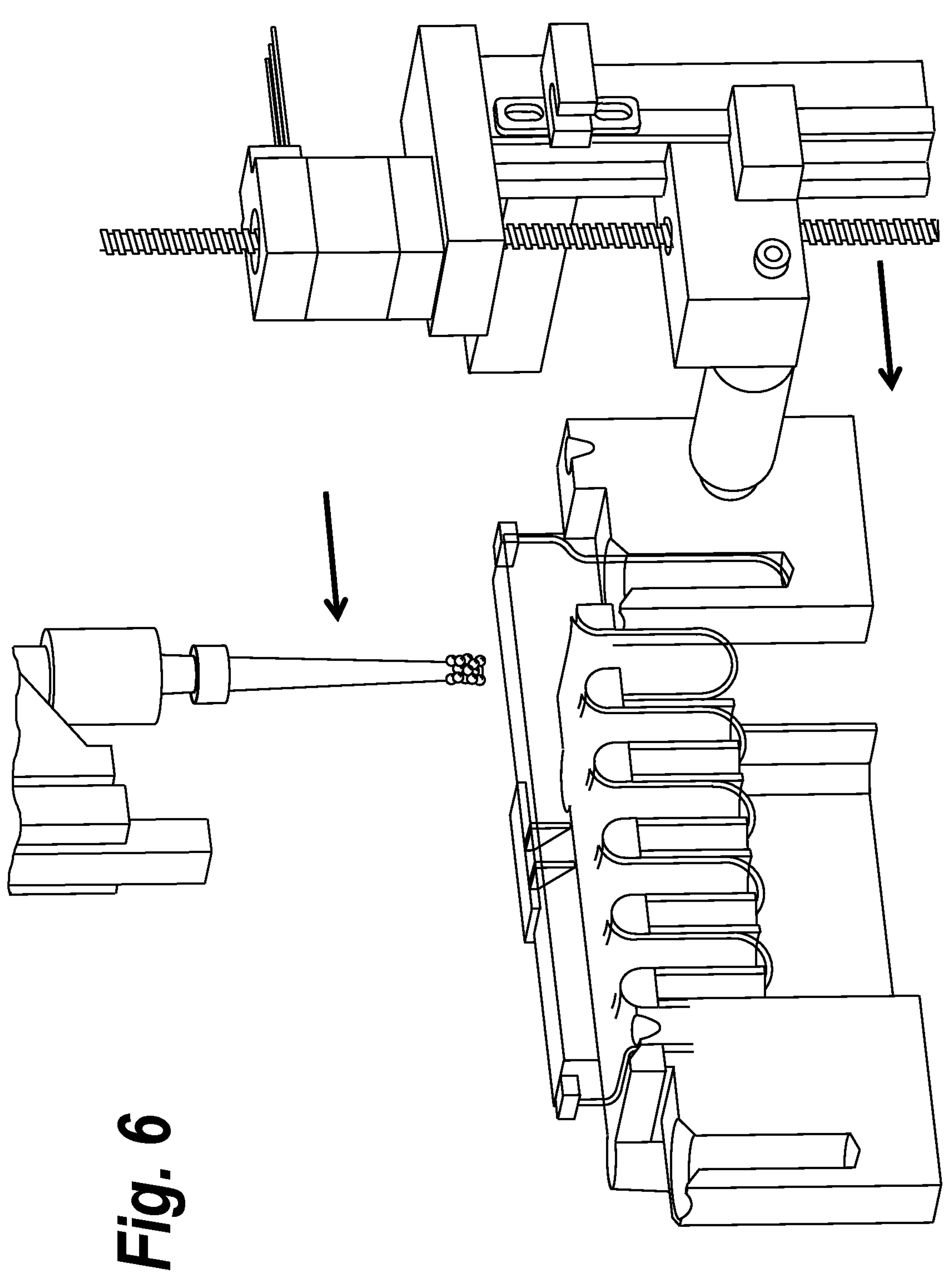
FIG. 6 illustrates horizontally moving the rotor mixer tip of the apparatus of FIG. 1 with the magnetic beads magnetically attached thereto towards a wash well.
Figures 7, 8, 9:
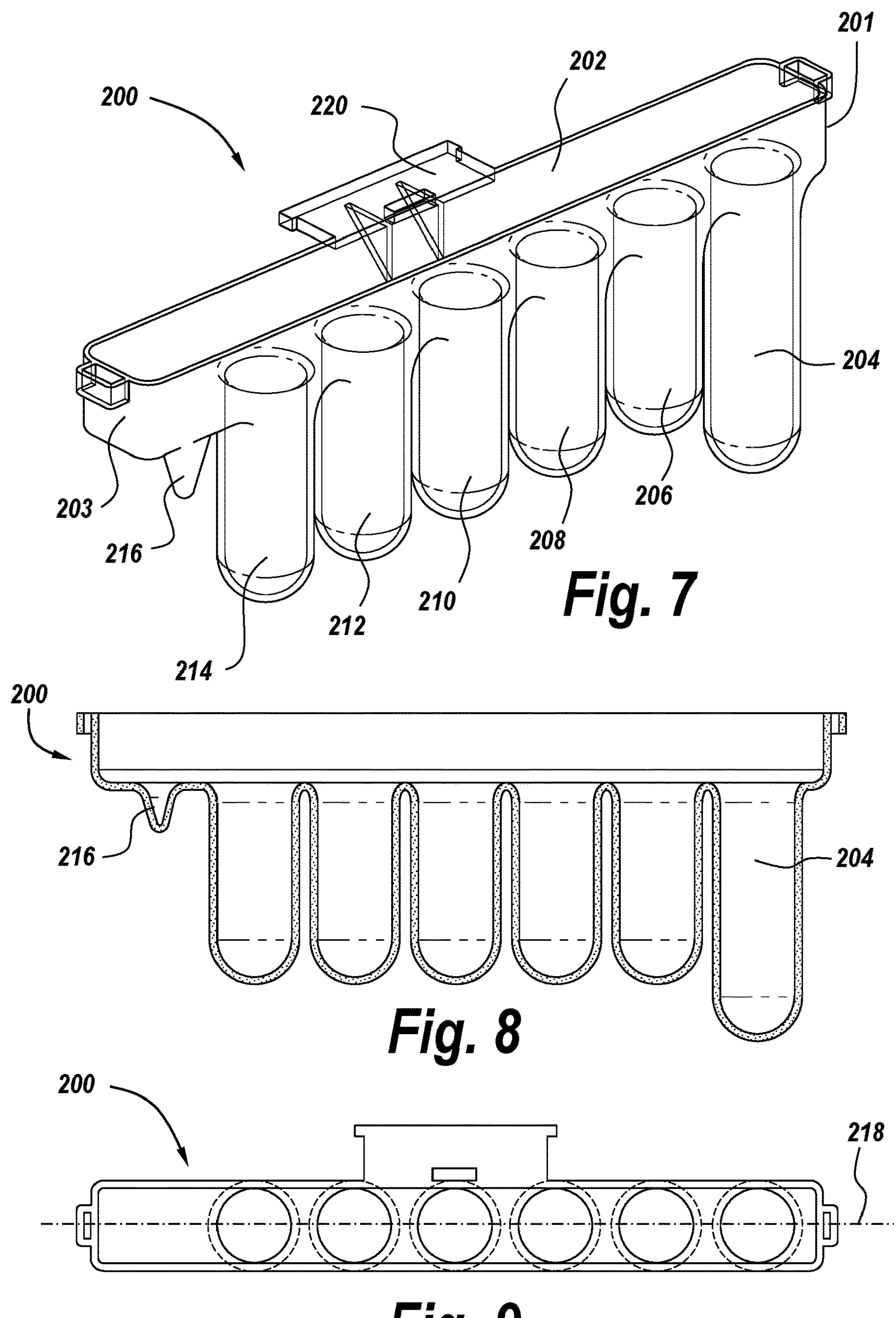
FIG. 7 is a perspective view of a multi-well plate according to the present disclosure.
FIG. 8 is a side section view of the multi-well plate of FIG. 7.
FIG. 9 is a top view of the multi-well plate of FIG. 7.
Figure 14:
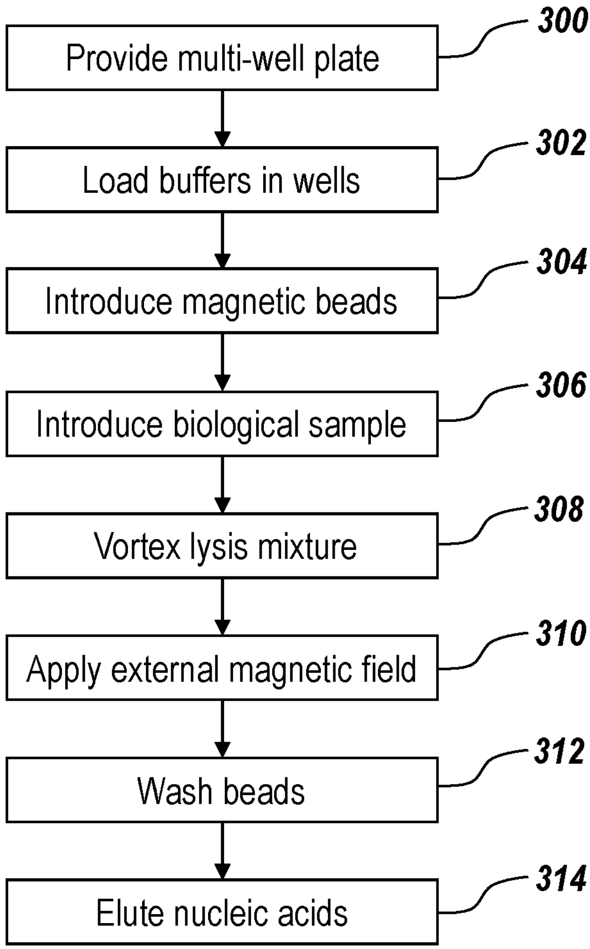
FIG. 14 is a flowchart of a method of sample lysis, purification, and elution.

In bead-washing step 312, vertical actuator 112 moves rotor mixer 102 in an upwardly direction, as illustrated in FIG. 5, thereby extracting tip 104 and the magnetic beads 402 attached thereto from lysis well 204. FIG. 6 shows the horizontal actuator (not shown) aligning rotor shaft 106 with one of wash wells, for example wash well 206. The external magnet 116 may also be moved horizontally in coordination with the rotor 102. Alternatively, the plate holder 222 may translate the multi-well plate 200 relative to the rotor and external magnet. Once properly aligned, the vertical actuator 112 moves the rotor mixer 102 in a downwardly direction, to immerse the magnetic tip 104 and the beads 402 attached thereto in a wash buffer contained in the wash well 206. A process similar to that executed within the lysis well 204 may then be carried out, including moving the external magnet 116 to a position adjacent the wash well, rotating the rotor to release the beads into the wash buffer and to allow the beads to gather on the wash well wall adjacent the external magnet, removing the external magnet, rotating the rotor again to resuspend the beads in the wash buffer, then ceasing rotation to allow the beads to reattach to the rotor magnetic tip 104. This process may also include vertically manipulating the external magnet to gather the beads in the bottom of the wash well prior to reintroducing the rotor and magnetic tip. This procedure can be repeated in any or all of the other wash wells 208, 210, 212, and 214. After a desired number of washing steps have been completed, the vertical and horizontal actuators immerse magnetic tip 104 and magnetic beads 402 in elution well 216, where nucleic acids elute from magnetic beads 402 into the elution buffer (step 314).

As anticipated, the contents of the lysis well 204 may be heated prior to the illustrated step 310 of applying an external magnetic field to an exterior surface of the lysis well. Following removal of the beads 402, liquid residues in the lysis well and the wash wells may be aspirated by a pipetting system and dispensed to a waste receptacle. Similarly, elution well 216 may undergo heating at any point prior to removal of the final nucleotide product solution.

The foregoing description has been directed to particular embodiments. However, other variations and modifications may be made to the described embodiments, with the attainment of some or all of their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. It will be understood that certain features and sub-combinations are of utility and may be employed without reference to other features and sub combinations and are contemplated within the scope of the claims. Accordingly, it will be understood that the following claims are not to be limited to the embodiments disclosed herein and can include practices other than those specifically described, and are to be interpreted as broadly as allowed under the law. Additionally, not all steps listed in the various figures need be carried out in the specific order described.

We claim:

1. A method of isolating nucleic acids from a biological sample, comprising:

providing a multi-well plate for performing nucleic acid isolation, the multi-well plate comprising:

a plurality of process wells arranged in a sequence on the multi-well plate, said sequence of process wells comprising:

a lysis well at a first end of the sequence of process wells, an elution well at an opposite second end of the sequence of process wells, and at least one wash well positioned intermediate the lysis well and the elution well along the sequence of process wells;

forming a lysis mixture by combining ingredients comprising the biological sample, a lysis buffer, and magnetic beads in the lysis well;

inserting a rotor mixer comprising a magnetic tip into the lysis well;

vortexing the lysis mixture by spinning the rotor mixer wherein the vortexing speed of the rotor mixer is sufficient to disperse the magnetic beads in the lysis mixture;

ceasing vortexing of the lysis mixture by stopping the spinning of the rotor mixer, whereby magnetic beads within the lysis mixture magnetically attach to the magnetic tip of the rotor mixer;

removing the rotor mixer tip with the magnetic beads magnetically attached thereto from the lysis well;

inserting the rotor mixer tip in the at least one wash well, wherein the at least one wash well contains a washing buffer, to wash the magnetic beads;

removing the rotor mixer from the at least one wash well; and immersing the rotor mixer tip with the magnetic beads magnetically attached thereto into the elution well, wherein the elution well contains an elution buffer, to elute the nucleic acids from the beads.

2. The method of claim 1, further comprising:

applying a magnetic field to a side wall of one of the plurality of process wells to attract the magnetic beads contained in said one of the plurality of process wells to the side wall thereof, whereby the magnetic beads are aggregated against the side wall, and removing the magnetic field after the magnetic beads have been attracted to the side wall.

3. The method of claim 2, further comprising moving the magnetic field in a downward direction after said magnetic field has been applied and before said magnetic field is removed, whereby the magnetic beads, attracted by the magnetic field applied to the side wall of the one of the plurality of process wells, travel down said side wall to come to rest at the bottom of the one of the plurality of process wells.

4. The method of claim 1, further comprising:

disposing the lysis buffer within the lysis well;

disposing the washing buffer within the at least one wash well, and disposing the elution buffer within the elution well.

5. The method of claim 1, further comprising heating the lysis well.

6. The method of claim 5, wherein the heating of the lysis well is imparted with a lysis well heating block.

7. The method of claim 1, further comprising heating the elution well.

8. The method of claim 7, wherein the heating of the elution buffer is imparted with an elution well heating block.

9. The method of claim 1, further comprising covering the rotor mixer tip with a disposable protective sleeve.

* * * * *